US006451601B1

(12) United States Patent
Baetge et al.

(10) Patent No.: US 6,451,601 B1
(45) Date of Patent: *Sep. 17, 2002

(54) TRANSIENTLY IMMORTALIZED CELLS FOR USE IN GENE THERAPY

(75) Inventors: Edward E. Baetge, St. Sulpice (CH); Shou Wong, Verona, WI (US); Philippe Dupraz, Crissier (CH); Bernard Thorens, Epalinges (CH)

(73) Assignee: Modex Therapeutiques, S.A. (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/823,177

(22) Filed: Mar. 29, 2001

Related U.S. Application Data

(63) Continuation-in-part of application No. 09/546,483, filed on Apr. 10, 2000.
(60) Provisional application No. 60/128,893, filed on Apr. 12, 1999.

(51) Int. Cl.$^7$ .................................................. C12N 5/08
(52) U.S. Cl. ....................... 435/366; 435/377; 435/405; 530/350; 536/23.4
(58) Field of Search ................................ 435/366, 377, 435/405; 530/350; 536/23.4

(56) References Cited

U.S. PATENT DOCUMENTS 6,015,709 A * 1/2000 Natesan ...................... 435/366

FOREIGN PATENT DOCUMENTS

| DE | 197 40 571 C1 | 3/1999 |
| WO | WO 97/05265 | 2/1997 |
| WO | WO 98/01542 | 1/1998 |
| WO | WO 98/04708 | 2/1998 |
| WO | WO 98/32866 | 7/1998 |
| WO | WO 98/42742 | 10/1998 |

OTHER PUBLICATIONS

Elliott and O'Hare, Intercellular Trafficking and Protein Delivery by a Herpesvirus Structural Protein, *Cell*, 88:223–33 (1997).
Harle–Bachor and Boukamp, Telomerase activity in the regenerative basal layer of the epidermis in human skin and in immortal and carcinoma–derived skin kerantinocytes, *Proc. Natl. Acad. Sci. USA*, 93:6476–81 (1996).
Jiang, et al., Telomerase expression in human somatic cells does not induce changes associated with a transformed phenotype, *Nature genetics*, 21:111–24 (1999).
Katakura, et al., Immortalization by Gene Transfection, *Methods in Cell Biol.*, 57:69–91 (1998).
Stauber and Pavlakis, Intracellular Trafficking and Interactions of the HIV–1 Tat Protein, *Virology*, 252:126–36 (1998).
Strahl and Blackburn, Effects of Reverse Transcriptase Inhibitors on Telomere Length and Telomerase Activity in Two Immortalized Human Cell Lines, *Molecular and Cellular Biology*, 16:53–65 (1996).
International Search Report dated Nov. 7, 2000.
Morales, et al., Absence of cancer–associated changes in human fibroblasts immortalized with telomerase, *nature genetics*, 21:115–18 (1999).
Virginia A. Zakian, Life and Cancer Without Telomerase, *Cell*, 91:1–3 (1997).
Nakamura and Cech, Reversing Time: Origin of Telomerase, *Cell*, 92:587–90 (1998).
Rojas, et al., Genetic engineering of proteins with cell membrane permeability, *Nature Biotechnology*, 16:370–75 (1998).
Phelan, et al., Intercellular delivery of functional p53 by the herpesvirus protein VP22, *Nature Biotechnology*, 16:440–43 (1998).
Fernandez and Bayley, Ferrying proteins to the other side, *Nature Biotechnology*, 16:418–20 (1998).
Dilber, et al., Intercellular delivery of thymidine kinase prodrug activating enzyme by the herpes simplex virus protein, VP22, *Gene Therapy*, 6:12–21 (1999).
Wu, et al, Direct activation of TERT transcription by c–MYC, *Nature Genetics*, 21:220–24 (1999).
Wang, et al., Myc activates telomerase, *Genes & Development*, 12:1769–1774 (1998).

* cited by examiner

*Primary Examiner*—James Ketter
(74) *Attorney, Agent, or Firm*—Ivor R. Elrifi; Christina Karnakis; Mintz, Levin, Cohn, Ferris, Glovsky and Popeo, P.C.

(57) ABSTRACT

The invention provides methods and compositions for expanding cells that are not abundant or are difficult to obtain in pure form in culture, are in short supply (e.g., human cells), or have brief lifetimes in culture, using fusion polypeptide. The fusion polypeptide has a first region containing a translocation carrier moiety having the function of a transport polypeptide amino acid sequence from, e.g., herpesviral VP22, HIV TAT, Antp HD, Arg repeats, or a cationic polymer, or from homologues or fragments thereof, and a second region with a polypeptide having cell immortalization activity, a polypeptide having telomerase-specific activity, or a polypeptide having telomerase gene activation activity. The resulting cells of the invention are suitable for use in cell therapy.

12 Claims, 8 Drawing Sheets

US 6,451,601 B1

TRANSIENTLY IMMORTALIZED CELLS FOR USE IN GENE THERAPY

CLAIM OF PRIORITY

This continuation-in-part application claims priority to United States provisional patent application 60/128,893, filed Apr. 12, 1999; U.S. patent application Ser. No. 09/546,483, filed Apr. 10, 2000, and PCT Publication WO 00/61617, filed Apr. 12, 2000.

FIELD OF THE INVENTION

The invention relates generally to tissue transplantation. More specifically, the invention relates to methods of increasing the replicative capacity of normally quiescent cells, such as normal somatic cells, by transient immortalization or transient telomerization, to produce cells suitable for cell therapy.

BACKGROUND OF THE INVENTION

Cell therapy is an emerging field for the treatment of medical disorders. Cells from various tissue sources have been contemplated for transplantation into mammals, including human, recipients for treatment of disease or tissue or organ replacement. Use of primary cells for transplantation requires continuous access to fresh sources of tissue. This is problematic, however, particularly if human cells are desired. Normal human somatic cells display a finite replicative capacity of 50–100 population doublings characterized by a cessation of proliferation in spite of the presence of adequate growth factors. The replicative capacity can be considerably less (10–50 population doublings) when these cells are placed in culture in vitro. This cessation of replication in vitro is variously referred to as cellular senescence or cellular aging.

To generate tissue in sufficient quantity for therapeutic use, cells are commonly immortalized, thus acquiring unlimited replicative capacity and avoiding cellular senescence. The identification of immortalizing genes and development of gene transfer methodologies permit generation of cell lines from cell types that are difficult to obtain in sufficient quantity or that have short lifetimes in culture. These immortalizing genes are typically generated by transfer of a virus or plasmid that contain an immortalizing gene. Cell immortalization increases the life span of a cell (especially in culture under replicative growth conditions), so that the resulting cell line is capable of being passaged many more times than the original primary cells.

The use of immortalized cells in cell therapy, however, can pose serious risks for patients, because immortalized cells are in many instances tumorigenic. Moreover, the exogenous DNA containing the nucleic acid capable of transforming the cells is commonly inserted into cells using infectious vectors, such as retroviral vectors. Virally infected cells also pose serious risks for patients, such as the potential of generating replication-competent virus during vector production; the potential recombination between the therapeutic virus and endogenous retroviral genomes, potentially generating infectious agents with novel cell specificities, host ranges, or increased virulence and cytotoxicity; and the potential independent integration into large number of cells, increasing the risk of tumorigenic insertional events.

Approaches to avoid these risks have focused on the removal of the genetic element when differentiation of the target cells is desired. One such approach involves the use of the Cre/loxP recombination system of bacteriophage P1. In the Cre/loxP procedure, the immortalizing gene, or oncogene, is flanked with recombinase recognition (loxP) sites for insertion, and subsequently removed via Cre-mediated deletion of the flanked gene segment. However, it is very difficult to prove the absence of residual immortalizing gene. Any leftover immortalizing gene would pose a serious risk to the recipient of the cell therapy, as it may allow these cells to continue to proliferate in the host after transplantation, and form a tumor. Accordingly, tissue from cells generated in this fashion is less desirable for cell therapy.

Thus, a need remains in the art for a method of cell proliferation that avoids the risks associated with the incorporation of exogenous immortalization genes in cells to be used for cell therapy.

SUMMARY OF THE INVENTION

The invention provides methods and compositions for generating cells that are not abundant, that are difficult to obtain in pure form in primary culture, that are in short supply (e.g., human cells), or that have brief lifetimes in culture. The invention relates to methods of conditional, transient cell proliferation in which immortalization or telomerization are initiated by the action of exogenously supplied molecules and terminated by the removal of these exogenously supplied molecules. Cells are proliferated in vitro for cell banking and, upon removal of the exogenous immortalizing or telomerizing fusion proteins, return to their non-proliferative state. The cells produced by the methods of the invention are suitable for transplantation and cell therapy. The methods of the invention can be used to proliferate any normally quiescent cell that can be induced to proliferate, such as normal somatic cells.

Provided in the invention are fusion proteins having a macromolecular translocation carrier moiety ("translocation moiety") coupled to amino acid sequences from cell immortalization proteins. Examples of translocation moieties include, but are not limited to, a transport polypeptide sequence from herpesviral VP22, a transport polypeptide sequence from human immunodeficiency virus (HIV) TAT, a homeodomain from the Antennapedia polypeptide ("Antp HD"), a polymer of L-arginine or D-arginine amino acid residues ("Arg repeats"), a polymer of cationic macromolecules ("cationic polymer"); or homologues or fragments thereof. Examples of proteins or polypeptides for cell immortalization include, but are not limited to, the 12S and 13S products of the adenovirus E1A genes, SV40 small T antigen and SN40 large T antigen (and subfragments and truncated versions thereof), papilloma viruses E6 and E7, the Epstein-Barr Virus (EBV), Epstein-Barr nuclear antigen-2 (EBNA2), human T-cell leukemia virus-1 (HTLV-1), HTLV-1 tax, Herpesvirus Saimiri (HVS), mutant p53, and the proteins from oncogenes such as myc, c-jun, c-ras, c-Ha-ras, h-ras, v-src, c-fgr, myb, c-myc, n-myc, and Mdm2. Also provided in the invention are fusion proteins having at least one translocation moiety from, e.g., a transport polypeptide amino acid sequence from herpesviral VP22, HIV TAT, Antp HD, Arg repeats, or a cationic polymer, or from homologues or fragments thereof, coupled with at least one amino acid sequence from proteins, or fragments thereof, with telomerase-specific activity. Examples of proteins with telomerase-specific activity include, e.g., telomerase, telomerase reverse transcriptase (TERT), p140, p150, p48, and p43, or homologues or fragments thereof.

In one embodiment of the invention, normally quiescent cells are transiently immortalized in order to proliferate these cells. Cells of interest are cultured in the presence of at least one fusion protein comprising a first translocation moiety having the transport function of, e.g., herpesviral VP22 protein, HIV TAT, Antp HD, Arg repeats, or a cationic polymer, and a second polypeptide having cell immortalization activity. The fusion protein is transported to the nucleus of the cells, and immortalizes the cells. The immortalized cells are expanded in the presence of at least one fusion protein. Once sufficient cells have been obtained, the fusion protein is removed from the growth medium, and the cells are cultured until they return to their original differentiated, non-immortalized state.

In another embodiment of the invention, normally quiescent cells are proliferated by transiently telomerizing these cells. Cells of interest are cultured in the presence of at least one fusion protein that includes a first component comprising a translocation moiety having the transport function of, e.g., herpesviral VP22 protein, HIV TAT protein, Antp HD, Arg repeats, or cationic polymer, or fragments or homologs thereof; and a second polypeptide having telomerase-specific activity. The fusion protein is transported to the nucleus of the cells where it synthesizes telomeric DNA at chromosomal ends, thereby preventing replicative senescence. The telomerized cells are expanded in the presence of at least one fusion protein of the invention. Once sufficient cells have been obtained, the fusion protein is removed from the growth medium, and the cells are cultured in a standard fashion in the absence of the exogenous immortalizing or telomerizing fusion proteins.

In yet another embodiment of the invention, a translocation moiety (such as VP22, TAT, Antp HD, Arg repeats, or cationic polymer, or fragments or homologs thereof) and an immortalizing gene (such as hTERT, SV40, etc.) are mixed together and applied to the cells.

In still another embodiment of the invention, normally quiescent cells are proliferated by transiently telomerizing these cells. Cells of interest are cultured in the presence of at least two fusion proteins: (1) a fusion protein comprising a translocation moiety (such as VP22, TAT, Antp HD, Arg repeats, or cationic polymer, or fragments or homologs thereof), and a polypeptide having cell immortalization activity; (2) a fusion protein comprising a translocation moiety (such as VP22, TAT, Antp HD, Arg repeats, or cationic polymer, or fragments or homologs thereof), and a polypeptide having telomerase-specific activity. The cells may be cultured in the presence of more than one type of translocation moiety-immortalization fusion or in the presence of more than one type of translocation moiety-telomerizing fusion, or both. The cells are expanded in the presence of the fusion proteins until sufficient cells with increased life span have been obtained. The fusion proteins are subsequently removed from the growth medium, and the cells are cultured until they return to their original differentiated, non-immortalized state.

The cells produced by the methods of the invention are not permanently immortalized (and thus are not tumorigenic or transformed) and are not virally infected. Accordingly, these cells, upon removal of the exogenous immortalizing or telomerizing fusion proteins, are suitable for transplantation and use in cell therapy.

In one embodiment of the invention, cellular immortalization is accomplished by direct transcriptional activation of telomerase reverse transcriptase, mediated by the addition of VP22-myc fusion protein. Wang, et al., 12 Genes & Dev. 1769–1774 (1998).

In another embodiment of the invention, a specific gene in a cell is transiently activated to specifically activate the expression of the endogenous gene of interest, and express the corresponding protein of interest. The proteins of interest include, but are not limited to, human growth hormone ("hGH"), erythropoietin ("EPO"), insulinotropin, insulin, leptin, hGCSF, Factor VIII, Factor VII, Factor IX, Factor X, and tissue-type plasminogen activator ("tPA").

DETAILED DESCRIPTION OF THE INVENTION

Figure 1:
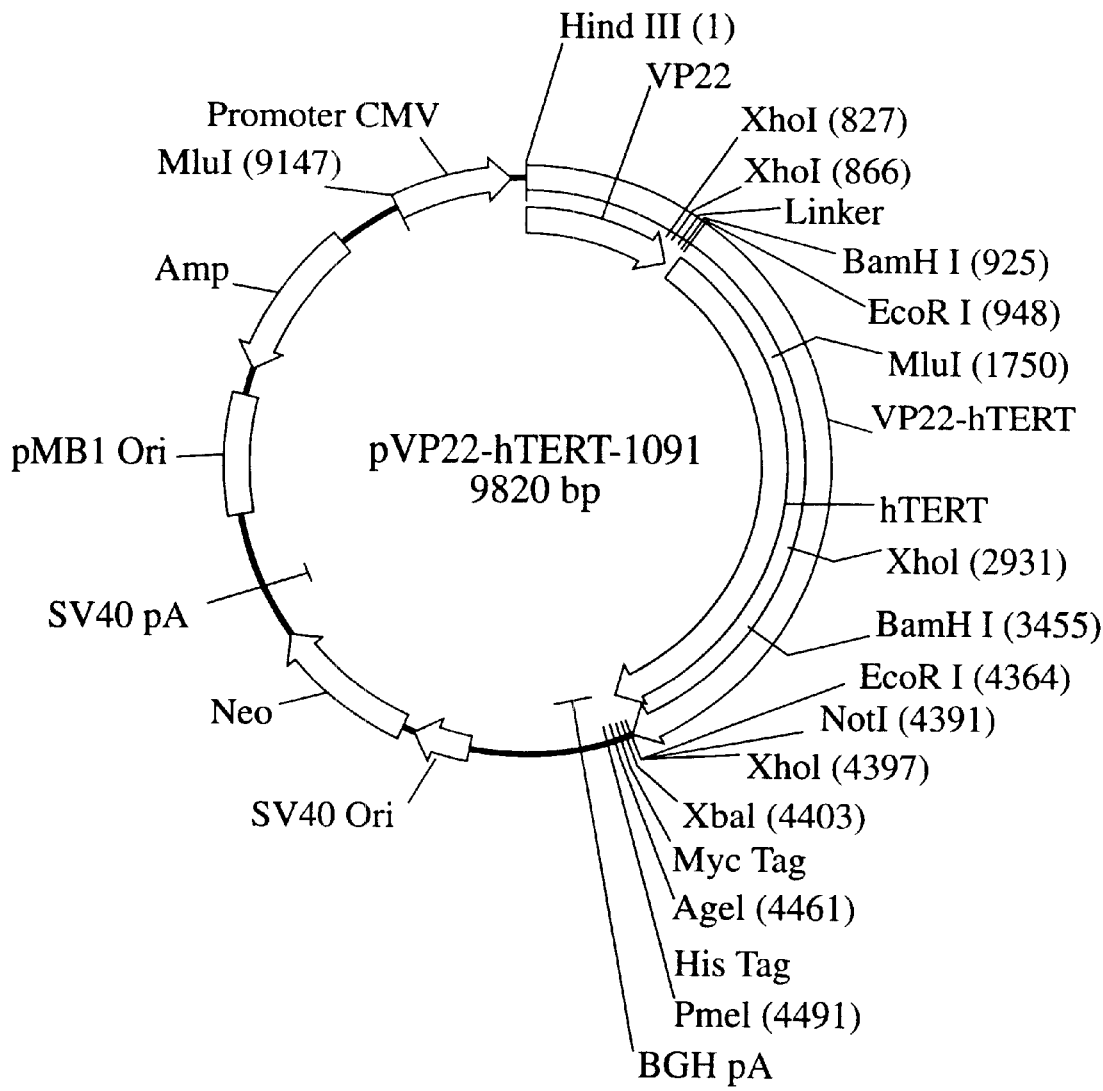
FIG. 1 is a plasmid map of pVP22-hTERT-1091.

The invention provides methods and compositions for use in conditional immortalization of primary mammalian cells. In one embodiment, the invention reports the coupling of a translocation moiety (including, but not limited to, VP22, TAT, Antp HD, Arg repeats, or cationic polymer, or fragments or homologs thereof) to an oncogene or immortalizing gene, such that eukaryotic or prokaryotic cells can efficiently produce the fusion protein.

The human telomerase gene (hTERT) is capable of immortalizing primary human fibroblast cells without causing the cells to become "transformed", (Morales, et al. 1999 *Nature Genetics* 21: 115–118; Jiang, et al. 1999 *Nature Genetics* 21: 111–114). In another embodiment, a human telomerase (hTERT) protein fused to a translocation moiety of the invention serves a similar immortalizing purpose when the fusion construct is carried across the cell membrane of appropriately exposed cells. By analogy, attaching any immortalizing protein, including but not limited to SV40, cMyc, E1A, E6, E7, ras, etc., to the carboxy terminus of the VP22 protein, or to any other translocation moiety of the invention, will allow these resulting fusion proteins to be efficiently transported into the nuclei of exposed primary cells.

The fusion proteins of the invention described herein, including all fusion constructs derived from a translocation moiety of the invention coupled to a protein of interest to be transported, such as an immortalizing protein, a telomerizing protein, or a transcription factor or the like that will activate an endogenous gene for an immortalizing protein or a telomerizing protein, are referred to in combination henceforth as "translocation fusion proteins."

In one embodiment, the invention provides for the conditional immortalization of human beta cells (for example, with SV40 TAG, myc, ras, etc.) in a transient fashion (for short periods of time or only during proliferation and expansion of the cells), for as long as the translocation moiety-immortalizing protein fusion construct is provided to the cells. Thus, the invention makes conditional immortalization possible without the direct use of DNA transfection or viral transduction.

Supernatants, extracts, or co-cultures from or with the cells producing a fusion construct of the invention can be used to deliver the oncogene, immortalizing protein, telomerase protein, or other protein of interest to the cell of choice. Alternatively, a translocation fusion protein of the invention can be purified and added to a culture medium as a medium supplement. Cells of interest are then treated with the supplemented culture medium containing the fusion protein additives. To obtain a differentiated final cell, the fusion protein additives are simply removed from the medium, such that culture medium without the fusion protein additive is provided to the cells.

The advantages of this approach is many. The advantages include the elimination of viral transduction or plasmid transfection of the human cell lines of interest. One can simply add the VP22-fusion proteins as a supplement to the tissue culture growth medium. In this way, the cells will be directly exposed to the immortalizing signals in culture without the need for permanent genetic modification of the cell with the oncogene or immortalizing gene sequences.

Another advantage of the invention compared to classical immortalizing techniques is the elimination of gene switch—and Cre/lox inactivation-based systems for the deactivation and elimination, respectively, of the introduced immortalizing gene sequences from the genome of the thus immortalized mammalian cells. Because no immortalizing gene nucleic acid sequence is ever introduced into the primary human cells, there is no need to add complicated gene switches (tet, ecdysone etc.) to turn off the expression of the immortalizing/transforming oncogene, or to flank the immortalizing gene with loxP sites for later excision of the oncogene by the addition of CRE recombinase. With the translocation moiety fusion protein systems of the invention, one simply removes the proteins responsible for cell expansion from the tissue culture medium and the cellular transport of immortalizing signals is halted. From a safety point of view there is considerably less concern about transferring potentially transformed human cells into the patient population. By contrast, it is very difficult with classical gene transfection-transduction methods to prove that the transforming gene sequence has been "completely" eliminated or turned off. In other words, with the traditional gene transformation approaches currently employed one can never be sure to completely inactivate every last one of the immortalizing genes originally inserted into the transplanted cells.

Another advantage of the present invention is that the removal of the translocation fusion protein(s) from the expanding cell culture medium increases the likelihood of a more efficient and rapid reversion of the expanding cells to a fully differentiated phenotype.

An additional advantage of the invention is that almost any protein of interest can be transported directly to the nucleus, without the need for gene delivery to the cell. The invention is especially advantageous for the conditional immortalization of human primary cells, such as pancreatic beta cells, hepatocytes, bone cells cartilage cells, fibroblasts, muscle cells, brain cells or fat cells, or any human cell which will benefit from the application of gene therapy techniques. As a result of efficient nuclear transport (as provided by fusion with a translocation moiety) the invention can also be used for the transient gene activation of specific endogenous genes in any cell line. When the fusion protein contains polypeptide sequences that transcriptionally activate specific gene expression of endogenous proteins, then the invention can also be used for the production of any protein of interest with out use of the coding sequence for that gene or protein. Examples of genes that might be endogenously activated through the use of VP22 or TAT fusion proteins are EPO, Factor VIII, leptin, hGH, insulin, etc. Thus, the invention can be used to transiently gene activate any primary or immortalized cell, for the production of said protein for any use.

The use of the invention can be transient, can be accomplished with any cell or cell type, and does not require DNA insertion into the promoter region upstream of the gene. We do not need any sequence information beyond that of the specific gene activation proteins. This avoids the use of gene activation of specific promoter sequences. Moreover, the invention can be utilized to develop a screen for transcriptional activators, which can be fused with a translocation moiety of the invention to screen for activators of any protein of interest.

In another embodiment, the translocation moiety of the invention is coupled to telomerase. The VP22-telomerase, TAT-telomerase, Antp HD-telomerase, Arg repeat-telomerase, or cationic polymer-telomerase fusion protein is transiently delivered to the cells of interest. Upon removal of the translocation fusion protein from the medium, the delivery process is stopped—but only after transiently "telomerizing" the chromosome tips, and extending replicative cell life for more than 50 population doublings or more. This delivery process does not require retention of the delivered gene sequence in any of our final products. Thus, the invention avoids the retention of viruses, Cre/lox, SV40, or telomerase in the final cell or device product.

In another embodiment, a translocation moiety of the invention is coupled to c-myc, which specifically induces telomerase activity via transcriptional activation, so that there is no need for the telomerase fusion protein (Wang, J. et al. 1998 *Genes & Devel.* 12, pp. 1769–1774).

Polypeptides having transportfunction. VP22 is a structural protein found in Herpes simplex type 1 virus (HSV). The herpesviral HSV-1 virion protein VP22 possesses an unusual intercellular trafficking mechanism (see PCT International patent application WO 97/05265; Elliott & O'Hare, 88 *Cell* 223–233 (1997)). The protein can efficiently transport itself through the membrane of cells via a non-classical Golgi-independent mechanism. The VP22 protein can transport itself into surrounding cells as the result of endogenous synthesis and secretion from producing cells or after exogenous application to naive cells. VP22 can spread throughout a monolayer of non-expressing cells, by transportation of VP22 from the cytoplasm of an expressing cell into neighboring cells. Interestingly, the VP22 protein is naturally targeted to the nucleus where it binds directly to chromatin and segregates to daughter cells after cell division. Furthermore, when fused to a variety of other proteins the VP22 protein can transport the fused proteins across cell membranes, thus carrying the attached proteins into the nucleus. More importantly, the VP22-fused proteins have been shown to retain biological activity in their chimeric state (i.e., fusion state) and to deliver the activity of the fused polypeptide directly into the exposed cell in a highly efficient manner. This VP22-fusion protein transport capability has recently been demonstrated for a variety of different proteins including Green Fluorescent protein, a 27 kDa fluorescent marker protein, (Elliott & O'Hare, 6 Gene Therapy 149–151, 1999); P-53, a 53 kDa cell cycle regulatory protein, (Phelean et al., 16 Nature Biotechnology 440–443, 1998); Thymidine Kinase, the 52 kDa enzyme serving as the converting enzyme in the pro-drug suicide protein combination routinely used in gene therapy trials; (Dilber et al., 6 Gene Therapy 12–21, 1999), and β-galactosidase, the 116 kDa bacterial enzyme widely employed as a reporter protein in gene expression studies (Invitrogen). In all of these studies the chimeric VP22 10 fusion proteins were efficiently transported into fusion-protein exposed cells. Most importantly, these translocation fusion proteins demonstrated the biological effects associated with each component of the coupled protein both in vitro and also in vivo for the VP220TK system.

Various other proteins have the capability to permeate cellular membranes by the addition of a membrane-translocating sequence (MTS). See, e.g., Rojas et al., 16 Nature Biotechnology 370–375, 1998. The MTS is a signal peptide with a hydrophobic region (h-region) used to deliver various peptides and proteins (cargo) across cell membranes in a nondestructive manner. See, e.g., Lin et al., 1995 J. Biol. Chem. 270: 14255–14258. The MTS construct can additionally include a nuclear localization sequence. See, e.g., Lin et al., 1995. HIV-1 TAT (Ensoli et al., 67 J. Virol 277–287 (1993); Fawell et al., 91 Proc. Natl. Acad. Sci. USA 664–668, 1994; Schwarze et al., 285 Science 1569–1572, 1999) and a small number of other non-viral proteins (Jackson et al, 89 Proc. Natl. Acad. Sci. USA 10691–10695, 1992) have also been attributed with intercellular trafficking properties, but none appears to demonstrate this phenomenon as strikingly as VP22, with the exception of denatured/renatured TAT protein (U.S. Pat. Nos. 5,652,122; 5,670,617; 5,674,980; 5,747,641; and 5,804,604, each of which is incorporated herein by reference), Antp HD (PCT Publications WO97/12912 and WO99/11809, each incorporated herein by reference), Arg repeats (Canadian Patent No. 2,094,658; U.S. Pat. No. 4,701,521, PCT Publication WO98/52614, each incorporated herein by reference), and cationic polymers (U.S. Pat. Nos. 4,701,521 and 4,847,240, each incorporated herein by reference). A further important property of VP22 is that, when applied exogenously to the medium of a cell monolayer, it can be taken up by those untransfected cells, where it accumulates in the cell nucleus.

The term "VP22" refers to protein VP22 of Herpes Simplex Virus (e.g., HSV1), and transport-active fragments and homologues thereof, including transport-active homologues from other herpes viruses including varicella zoster virus ("VZV"), equine herpes virus ("EHV") and bovine herpes virus ("BHV"); modified and mutant proteins and fusion polypeptides and coupling products having homology therewith and a transport function corresponding to a transport function of VP22 from HSV1. In context "VP22" also relates to nucleic acid sequences encoding any of the above VP22 polypeptides whether in the form of naked DNA or RNA, or of a vector, or of larger nucleic acid sequences including such sequences as sub-sequences.

Sub-sequences of herpesviral VP22 protein with transport activity, and methods of testing these, have been described elsewhere. For example, see PCT International patent applications WO 97/05265, WO 98/04708, and WO 98/32866, each of which is incorporated herein by reference. Sub-sequences of herpesviral VP22 protein with transport activity include polypeptides corresponding to amino acids 60–301 and 159–301 of the full HSV1 VP22 sequence (aa 1–301). A polypeptide consisting of amino acid residues ("aa") 175–301 of the VP22 sequence has markedly less transport activity, and is less preferred in connection with the invention. Accordingly, the invention relates in one aspect to coupled and fusion proteins comprising a sub-sequence of VP22 containing a sequence starting preferably from about aa 159 (or earlier, towards the N-terminal, in the native VP22 sequence), to about aa 301, and having (relative to the full VP22 sequence) at least one deletion of at least part of the VP22 sequence which can extend, for example, from the N-terminal to the cited starting point, e.g., a deletion of all or part of the sequence of about aa 1–158. Less preferably, such a deletion can extend further in the C-terminal direction, e.g., to about aa 175. For example, partial sequences in the range from about aa 60–301 to about aa 159–301 are preferred.

VP22 sequences, as contemplated herein, extend to homologous proteins and fragments based on sequences of VP22 protein homologues from other herpesviruses. For example, corresponding derivatives and VP22-homologue sequences have been obtained from VZV (e.g., all or homologous parts of the sequence from aa 1–302), from MDV (e.g., all or homologous parts of the sequence from aa 1–249), and from BHV (e.g., all or homologous parts of the sequence from aa 1–258) (see PCT International patent applications WO 97/05265, WO 98/04708, and WO 98/32866). The sequences of the corresponding proteins from HSV2, VZV, BHV and MDV are available in public protein/nucleic acid sequence databases. Thus, for example, within the EMBL/GenBank database, a VP22 sequence from HSV2 is available as gene item UL49 under accession no. Z86099 containing the complete genome of HSV2 strain HG52; the complete genome of VZV including the homologous gene/protein is available under accession numbers X04370, M14891, M16612; the corresponding protein sequence from BHV is available as "bovine herpesvirus 1 virion tegument protein" under accession number U21137; and the corresponding sequence from MDV is available as gene item UL49 under accession number LI 0283 for "gallid herpesvirus type 1 homologous sequence genes". In these proteins, especially those from HSV2 and VZV, corresponding deletions can be made, e.g. of sequences homologous to aa 1–159 of VP22 from HSV1. These above cited sequences are hereby incorporated herein by reference. Homologies between the various VP22 polypeptides are readily accessible by the use of standard algorithms and software, for example those mentioned in PCT International patent application WO 95/12673, pg. 9.

Furthermore, chimeric VP22 proteins and protein sequences are also useful within the context of the invention, e.g., a protein sequence from VP22 of HSV1 for part of which a homologous sequence from the corresponding VP22 homologue of another herpesvirus has been substituted. For example, into the sequence of polypeptide 159–301 from VP22 of HSV1, C-terminal sequences can be substituted from VP22 of HSV2 or from the VP22 homologue of BHV.

Deletion of the 34-amino acid C-terminal sequence from VP22 of HSV1 has been reported to abolish transport-activity (see PCT International patent applications WO 97/05265, WO 98/04708, and WO 98/32866). Thus this sequence region contains essential elements for transport activity. According to a preferred embodiment of the invention, there are provided coupled and fusion polypeptides comprising the 34-amino acid C-terminal sequence from VP22, or a variant thereof, together with a sequence from: (a) a protein or polypeptide for cell immortalization; (b) a protein or polypeptide that has telomerase-specific activity; or (c) a protein or polypeptide for the activation of a specific endogenous gene. These are provided for example for use by administration in the form of protein to cells that will take them up. Coupled products of modified terminal fragments having at least one mutation insertion or deletion relative to the C-terminal 34 amino acid sequence of HSV1 VP22 are also provided. According to an alternative preferred embodiment of the invention, the fusion polypeptides comprises the 34-amino acid C-terminal sequence from VP22, or a variant thereof, together with a nucleic acid sequence (DNA or RNA) encoding: (a) a protein or polypeptide for cell immortalization; (b) a protein or polypeptide that has telomerase-specific activity; or (c) a protein or polypeptide for the activation of a specific gene.

Sequences necessary for transport activity have also been reported to contain one or a plurality of amino acid sequence motifs or their homologues from the C-terminal sequence of VP22 of HSV1 or other herpesviruses, which can be selected from RSASR (SEQ ID NO:3), RTASR (SEQ ID NO:4), RSRAR (SEQ ID NO:5), RTRAR (SEQ ID NO:6), ATATR (SEQ ID NO:7), and wherein the third or fourth residue A can be duplicated, e.g., as in RSAASR (SEQ ID NO:8).

Translocation moieties, as contemplated herein, extend to VP22 sequences described above and sequences from proteins with translocation properties similar to VP22. Proteins with translocation properties similar to VP22 include, but are not limited to, the MTS (membrane translocating sequence) 12 amino acid region from Kaposi fibroblast growth factor and a similar 11 amino acid region of the HIV TAT protein (Rojas et al., 16 *Nat. Biotechnol.* 370–375 (1998) and Schwarze et al., 285 *Science* 1569–1572 (1999), respectively). Also included are the homeodomain sequence from Antennapedia (Antp HD, described, e.g., in PCT Publications WO97/12912 and WO99/11809) and sequences containing Arg repeats (described, e.g., in Canadian Patent No. 2,094,658; U.S. Pat. No. 4,701,521; PCT Publication WO98/52614). In addition, cationic polymers with translocation properties similar to VP22, i.e., macromolecules that at a neutral pH contain positively charged chemical groups sufficient to enhance cellular uptake of molecules covalently bound to it, are included in the invention. Examples of contemplated cationic polymers include, but are not limited to, such as macromolecules that contain sequential portions or spatial arrangements of positive charges, e.g., homopolymers or copolymers of poly(amino acids) such as poly-L-lysine, poly-D-lysine, poly-L-arginine, poly-D-arginine, and of non-amino acids such as polysaccharides or uncharged polymers substituted with side chain amines, wherein the resulting positively charge is sufficient to confer on the resulting macromolecule a translocation property similar to VP22 (see, e.g., U.S. Pat. Nos. 4,701,521 and 4,847,240).

Fusion Proteins. In use, many of the compositions described herein can be expressed as fusion proteins in a first part of the target population of cells, exported therefrom, and harvested. The harvested translocation fusion protein is then placed in a growth medium where it is taken up by a second part of the target population of cells not directly producing the protein.

A translocation fusion polypeptide as described herein can be transported to a target population of cells, by introducing a polynucleotide or other vector encoding the fusion polypeptide into a first population of cells (e.g., by transfection or microinjection), expressing the encoding polynucleotide to produce the translocation fusion polypeptide, causing it to be exported from the first population of cells, harvested, and introduced to a second population of cells via the growth medium.

Translocation moieties of the invention, or functional sub-sequences thereof, optionally with an additional polypeptide tail for coupling, can be linked to other proteins or nucleic acid by chemical coupling in any known suitable standard manner. Coupling or fusion of an amino acid sequence with the transport function of a translocation moiety, such as VP22 protein, Antp HD, Arg repeat, cationic polymer, or TAT protein, can provide a useful cell delivery construct for proteins of the kinds mentioned.

The term "fusion proteins" include terms such as "coupled proteins," "coupling products," and "fusion products." Preferably the coupled proteins are fusion proteins, which can conveniently be expressed from approximately in-frame-fused gene-coding sequences in known suitable host cells. Corresponding polynucleotide sequences can be prepared and manipulated using elements of known and standard recombinant DNA techniques and readily available adaptations thereof. However, chemically-coupled products can for certain applications be used if desired, and can be prepared from the individual protein components according to any of a variety of chemical coupling techniques known in the art.

Fusion proteins can be formed and used in ways analogous to or readily adaptable from standard recombinant DNA techniques. The polynucleotide can be comprised in an open reading frame operably linked to a suitable promoter sequence, and form part of an expression vector, e.g., comprising the polynucleotide carried in a plasmid. The expression vector can, for example, be a recombinant virus vector or a non-viral transfection vector. The vectors can, for example, be analogs or examples of those vectors mentioned or described in PCT International patent application WO 97/05265, or of those mentioned or described in PCT International patent applications WO 92/05263, WO 94/21807, or WO 96/26267. For nucleotide sequences that are capable of being transcribed and translated to produce a functional polypeptide, degeneracy of the genetic code results in a number of nucleotide sequences that encode the same polypeptide. The invention includes all such sequences.

Products described herein can be used according to the invention as transportable proteins capable of being taken up by a target population of cells, e.g., so that an effector function corresponding to the polypeptide sequence coupled to the translocation moiety, from among the kinds mentioned above, can take place within the target cells that have taken up the product. Thus, for example, the target cells may be immortalized in a case where the polypeptide or nucleotide sequence is from an immortalizing agent or from an activator of an immortalizing agent, or obtain an extended replicative life span where the polypeptide or nucleotide sequence is from telomerase, or from a telomerase activator. In use, many of the products described herein can be expressed as fusion proteins in a first part of the target population of cells, exported therefrom, and harvested. The fusion protein is then placed in a growth medium where it is taken up by a second part of the target population of cells not directly producing the protein.

A translocation fusion protein, as described herein, can be transported to a first population of cells by introducing a polynucleotide or other vector encoding the fusion polypeptide into a first part of the target population of cells (e.g., by transfection or microinjection), expressing the encoding polynucleotide to produce the fusion polypeptide, thereby to cause it to be exported from said first part of said target population, harvested, and introduced to a second part of the target population of cells via the growth medium. Fusion protein (including chemically coupled products) can also be transported into a target population of cells by directly exposing the cells to a preparation of the fusion protein, thereby to cause the target cells to take them up.

Among the derivatives of VP22 that can be used according to aspects of the invention as transport active substances and for coupling with materials to be transported, for the purposes set forth elsewhere herein, are peptides comprising a transport-active functional sequence from the C-terminal section of VP22. Among the derivatives of Antennapedia that can be used according to aspects of the invention as transport active substances and for coupling with materials to be transported, for the purposes set forth elsewhere herein, are peptides comprising a transport-active functional sequence from the homeodomain section of Antennapedia. Among the derivatives of an Arg repeat that can be used according to aspects of the invention as transport active substances and for coupling with materials to be transported, for the purposes set forth elsewhere herein, are peptides containing a transport-active functional sequence of contiguous or partially contiguous segments of at least 5, 6, 7, 8, 9, 10, 11, 12, 15, 20, 25, 50, 100, or 1000 arginine residues, wherein the arginine residues may be of the D-form, the L-form, or mixtures of each. Likewise, derivatives of cationic polymers with the above functions may contain transport-active functional sequence of contiguous or partially contiguous segments of at least 5, 6, 7, 8, 9, 10, 11, 12, 15, 20, 25, 50, 100, or 1000 lysine residues, wherein the lysine residues may be of the D-form, the L-form, or mixtures of each. The above described Arg repeats, cationic polymers of lysine residues, or both, may be expressed from a nucleic acid encoding the desired residues coupled with a second nucleic acids encoding the remaining component to create a fusion protein of the invention, or they may be synthesized and conjugated to a second component of the invention to create the fusion protein of interest.

In an example embodiment, the coupling products or fusion proteins based on VP22 can have a range of molecular sizes. The products can in practice be for example up to about 70 kDa or more, e.g., 90 kDa or 100 kDa or more in respect of the size of the protein to be coupled or fused to VP22. The embodiments of the invention include examples where the fusion peptide is at least about 13 residues long, or more than about 12 amino acid residues long. The proteins to be fused can sometimes also be more than about 27 or 32 kDa. The coupled polypeptide or fusion protein, including the VP22 component can have sizes greater than 120 kDa, e.g., up to about 180 kDa or 200 kDa.

It is sometimes preferred that the translocation moiety sequence is fused at its N-terminus to the sequence of the chosen other protein of one of the kinds mentioned herein. Alternatively, C-terminal fusions of the translocation moiety can sometimes be correspondingly preferred.

In the translocation fusion polypeptides of the invention, mutations of the constituent amino acid sequences can be incorporated in the fusion polypeptides and other coupled proteins. Included here are proteins having mutated sequences such that they remain homologous, e.g. in sequence, function; and antigenic character or other function, with a protein having the corresponding parent sequence. Such mutations can preferably for example be mutations involving conservative amino acid changes, e.g., changes between amino acids of broadly similar molecular properties. For example, interchanges within the aliphatic group alanine, valine, leucine and isoleucine can be considered as conservative. Sometimes substitution of glycine for one of these can also be considered conservative. Interchanges within the aliphatic group aspartate and glutamate can also be considered as conservative. Interchanges within the amide group asparagine and glutamine can also be considered as conservative. Interchanges within the hydroxy group serine and threonine can also be considered as conservative. Interchanges within the aromatic group phenylalanine, tyrosine and tryptophan can also be considered as conservative. Interchanges within the basic group lysine, arginine and histidine can also be considered conservative. Interchanges within the sulfur-containing group methionine and cysteine can also be considered conservative. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine. In other respects, mutated sequences can comprise insertions such that the overall amino acid sequence is lengthened while the protein retains transport properties. Additionally, mutated sequences can comprise random or designed internal deletions that shorten the overall amino acid sequence while the protein retains transport properties.

The mutated protein sequences can additionally or alternatively be encoded by polynucleotides that hybridize under stringent conditions with the appropriate strand of the naturally-occurring polynucleotide encoding the parent protein, and can be tested for positive results in known functional tests relevant to the parent protein. 'Stringent conditions' are sequence dependent and will be different in different circumstances. Generally, stringent conditions can be selected to be about 5° C. lower than the thermal melting point ($T_M$) for the specific sequence at a defined ionic strength and pH. The $T_M$ is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may affect the stringency of hybridization (including, among others, base composition and size of the complementary strands), the presence of organic solvents and the extent of base mismatching, the combination of parameters is more important than the absolute measure of any one.

Translocation fusion proteins of the invention can be easily purified using a poly-His (poly-histidine) tag. Systems for producing fusion proteins containing poly-His tags are commercially available (Xpress, Invitrogen, San Diego Calif.; HisTrap kit, Pharmacia Biotech Inc., Piscataway, N.J.).

Coupling with immortalizing proteins. A common approach to lengthening the life span of a cell is to transfer a virus or a plasmid that contains one or more immortalizing genes. Cell immortalization increases the life span of a cell, and the resulting cell line is capable of being passaged many more times than the original cells. However, irreversibly transformed, tumorigenic human cells may form colonies in soft agar and also may form tumors in nude mice. These cells are unsuitable for direct cell therapy or any assay of fully differentiated cell functions.

In one useful class of embodiments of the invention, VP22 can be coupled with known proteins or polypeptides that cause cells to be immortalized. Immortalizing genes are well known in the art. See, e.g., Katakura et al., *Methods Cell Biol.* 57: 69–91 (1998). Immortalizing proteins or polypeptides include, but are not limited to, the 12S and 13S products of the adenovirus E1A genes, SV40 small and large T antigens, papilloma viruses E6 and E7, the Epstein-Barr Virus (EBV), Epstein-Barr nuclear antigen-2 (EBNA2), human T-cell leukemia virus-1 (HTLV-1), HTLV-1 tax, Herpesvirus Saimiri (HVS), mutant p53, and the proteins from oncogenes such as myc, c-jun, c-ras, c-Ha-ras, h-ras, v-src, c-fgr, myb, c-myc, n-myc, and Mdm2.

In an example of the invention concerned with cell immortalization, VP22 is coupled with the oncoprotein myc (v-myc or c-myc). Thus, according to one embodiment of the invention, there is provided a fusion protein comprising an amino acid sequence with the transport function of herpesviral VP22 protein and a sequence with the immortalization functionality of myc. In a preferred embodiment, the fusion protein includes substantially the full length myc sequence and substantially the full length VP22 sequence.

Fusion with a translocation moiety of the invention is useful for delivery of an agent for immortalization such as myc. Where the description given herein refers to myc and related peptides; it will be understood that, where the context admits, alternative immortalizing agents, such as for example those myc analogues and other immortalizing agents mentioned and referred to herein, are also contemplated, as are, more generally, alternative fusion or coupling partners for translocation moieties, of any of the other types mentioned herein. Once expressed in a subpopulation of expressing cells, harvested, and administered to the growth medium of cells of interest, such a fusion protein can be transported by the translocation moiety's transport mechanism to a significant portion of the target normal somatic cells so exposed, and the foreign attached polypeptide will then transiently immortalize these normal cells.

Also provided by this aspect of the invention are corresponding polynucleotides encoding a fusion polypeptide that include a sequence with the transport function of a translocation moiety of the invention, e.g., herpesviral VP22 protein, and a sequence with the human or other mammalian cell proliferating function of an oncogene, e.g., myc. The polynucleotide can be created in an open reading frame operably linked to a suitable promoter sequence.

The resulting polynucleotide forms an "expression cassette" and can, according to contemplated examples of the invention, form part of an expression vector, e.g., comprising the polynucleotide carried in a plasmid. The expression vector can be for example a virus or a non-viral transfection vector.

Coupling with telomerase. Telomeres are specialized structures at the ends of eukaryotic chromosomes and appear to function in chromosome stabilization, positioning, and replication. Blackburn & Szostak, 53 *Ann. Rev. Biochem.* 163–194 (1984); Zakian, 23 *Ann. Rev. Genetics* 579–604 (1989); Blackburn, 350 *Nature* 569–573 (1991). In all vertebrates, telomeres consist of hundreds to thousands of tandem repeats of 5'-TTAGGG-3' sequence and associated proteins (Blackburn 1991 *Nature* 350: 569–573; Moyzis et al., 1988 *Proc. Natl. Acad. Sci.* 85: 6622–6626). Southern blot analysis of chromosome terminal restriction fragments (TRF) provides the composite lengths of all telomeres in a cell population (Harley et al., 3445 *Nature* 458–460 (1990); Allsopp et al., 89 *Proc. Natl. Acad. Sci. USA* 10114–10118 (1992); Vaziri et al., 52 *Am. J Human Genetics* 661–667 (1993)). In all normal somatic cells examined to date, TRF analysis has shown that the chromosomes lose about 50–200 nucleotides of telomeric sequence per cell division, consistent with the inability of DNA polymerase to replicate linear DNA to the ends (Watson, 239 *Nature New Biology* 197–201 (1972)).

This shortening of telomeres has been proposed to be the mitotic clock by which cells count their divisions (Harley, 256 *Mut. Res.* 271–282 (1991)), and a sufficiently short telomeres may be the signal for replicative senescence in normal cells (Hastie et al., 346 *Nature* 866–868 (1990); Lindsey et al., 256 *Mut. Res.* 45–48 (1991); Wright & Shay, 8 *Trends Genetics* 193–197 (1992)). In contrast, the vast majority of immortal cells examined to date show no net loss of telomere length or sequence with cell divisions, suggesting that maintenance of telomeres is required for cells to escape from replicative senescence and proliferate indefinitely (Counter et al., 11 *EMBO* 1921–1929 (1992); Counter et al., 91 *Proc. Natl. Acad. Sci.* USA 2900–2940, 1994).

Telomerase, a unique ribonucleoprotein DNA polymerase, is the only enzyme known to synthesize telomeric DNA at chromosomal ends using as a template a sequence contained within the RNA component of the enzyme (Greider & Blackburn, 43 *Cell* 405–413 (1985); Greider & Blackburn, 337 *Nature* 331–337 (1989); Yu et al., 344 *Nature* 126–132 (1990); Blackburn, 61 *Ann. Rev. Biochem.* 113–129 (1992)). With regard to human cells and tissues, telomerase activity has been identified in immortal cell lines and in ovarian carcinoma but has not been detected in mortal cell strains or in normal non-germline tissues (Morin, 59 *Cell* 521–529, 1989). Together with TRF analysis, these results suggest telomerase activity is directly involved in telomere maintenance, linking this enzyme to cell immortality.

Expression of the human telomerase catalytic component (hTERT) has recently been studied in human somatic cells. Jiang, et al., 21 *Nature Genetics* 111–114 (1999). Telomerase expression in normal somatic cells did not appear to induce changes associated with a malignant phenotype such as abnormal growth control or oncogenic transformation. The absence of cancer-associated changes was also reported in human fibroblasts immortalized with telomerase. Morales, et al., 21 *Nature Genetics* 115–118 (1999). It was demonstrated that the introduction of telomerase into normal human somatic cells does not lead to growth transformation, does not bypass cell-cycle induced checkpoint controls and does not lead to genomic instability of these cells. Methods for detecting telomerase activity, as well as for identifying compounds or polypeptides that regulate or affect telomerase activity, together with methods for therapy or diagnosis of cellular senescence and immortalization by controlling or measuring telomere length and telomerase activity, have also been described (see PCT International patent application WO 93/23572). The identification of compounds affecting telomerase activity provides important benefits to efforts at treating human disease. Compounds that stimulate or activate telomerase activity (such as myc) can be fused to translocation moieties of the invention to inhibit cell senescence and increase the life span of the cell.

In a further class of embodiments of the invention, translocation moieties of the invention, or functional subsequences thereof, can be usefully coupled or fused with telomerase, or other enzyme or functional fragment thereof known as applicable for a similar purpose. The coupling product can penetrate into cells that are to be treated. Such translocation fusion proteins made up of translocation moiety-telomerase coupling products are used in the extension of the replicative life span of the target cell. The telomerase functions to stabilize the telomeres of the cell and arrest cellular senescence. See, e.g., U.S. Pat. No. 5,837,857.

Transient immortalization or telomerization of cells. According to one aspect of the invention, normally quiescent cells are transiently immortalized in order to proliferate these cells. Cells of interest are cultured in the presence of a fusion protein comprising a first polypeptide having: (1) a translocation moiety and (2) a polypeptide having cell immortalization activity. The resulting fusion protein is transported to the nucleus of the cells, and immortalizes the cells. The immortalized cells are expanded in the presence of the fusion protein. Once sufficient cells have been obtained, the fusion protein is removed from the growth medium, and the cells are cultured until they return to their original, non-immortalized state. More than one oncogene or immortalizing fragment may be required.

According to another aspect of the invention, normally quiescent cells are proliferated by transiently telomerizing these cells. Cells of interest are cultured in the presence of a fusion protein comprising: (1) a translocation moiety and (2) a polypeptide having telomerase-specific activity. The resulting fusion protein is transported to the nucleus of the cells where it synthesizes telomeric DNA at chromosomal ends, thereby preventing replicative senescence. Once sufficient cells have been obtained, the translocation fusion protein is removed from the growth medium, and the cells are cultured according to standard techniques, in absence of the fusion proteins.

According to yet another aspect of the invention, normally quiescent cells are proliferated by transiently immortalizing and telomerizing these cells. Cells of interest are cultured in the presence of two fusion proteins: (1) a fusion protein comprising a first part containing a translocation moiety of the invention and a second part containing a polypeptide having cell immortalization activity; and (2) a fusion protein comprising a first part containing a translocation moiety of the invention and a second part containing a polypeptide having telomerase-specific activity, or telomerase gene activation activity. The cells are expanded in the presence of the fusion proteins until sufficient cells have been obtained. The cells are then subsequently cultured according to standard techniques, in absence of the fusion proteins.

Transient gene activation. In another embodiment of the invention, a specific gene in a cell is transiently activated to specifically activate the expression of the endogenous gene of interest. The genes of interest include, but are not limited to, hGH, FAC VIII, FAC VII, FAC IX, FAC X, EPO, insulin, and TPA.

Equivalents. From the foregoing detailed description of the specific embodiments of the invention, it should be apparent that unique methods of increasing the replicative capacity of normally quiescent cells have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For instance, the choice of the particular translocation moiety having the transport function similar to herpesviral VP22 protein, or the particular polypeptide having cell immortalization activity, or the particular polypeptide having telomerase-specific activity, is believed to be a matter of routine for a person of ordinary skill in the art with knowledge of the embodiments described herein.

The details of one or more embodiments of the invention have been set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate the preferred embodiments of the invention. These EXAMPLES should in no way be construed as limiting the scope of the invention, as defined by the appended claims.

EXAMPLE 1

Construction of the VP22-hTERT FUSION

Materials. Taq polymerase and all restriction, modifying, and enzymes were purchased from Life-Technologies (Basel, Switzerland). The expression vector pCEP4, TA- and Cloning kits were obtained from Invitrogen Corporation (Carlsbad, Calif., U.S.A.). The Quick-Clone CDNA from human testis, lymphoma and HeLa cells, GC-Melt Genomic and cDNA PCR kits were purchased from ClonTech (Basel, Switzerland). The TRAPeze assay kit was obtained from Oncor (Basel, Switzerland).

Oligonucleotides. The following oligonucleotides were custom synthesized (Life-Technologies or Microsynth) for use as PCR primers in the cloning of the hTERT cDNA:

5'-ATATATGCTAGCGCCACCATGCCGCGCGCTCCC-CGCTGCC-3' (SEQ ID NO:1).

5'-ATATATGAATTCAGTCCAGGATGGTCTTGAAGT-CTGAGGGC-3' (SEQ ID NO:2).

RT-PCR amplification of 293T CDNA using Taq polymerase with these primers produced a 3417 base-pair product. Diagnostic restriction digestion patterns confirmed that this 3417-bp RT-PCR product was indeed derived from the hTERT cDNA. The product was subsequently subcloned into pCR2.1 by using the TOPO-TA cloning kit (Invitrogen). Nucleotide sequence determination of the resulting clone, pCR2.1-hTERT-1007, demonstrated that the cloned hTERT had the correct nucleotide sequence when compared to the published hTERT nucleotide sequence. Nakamura et al., 1997; GenBank Accession Number AF05950.

Construction of the VP22-hTERT Chimera Fusion Gene. A 3416-bp EcoRI fragment containing the intact hTERT cDNA was excised out of pCR2.1-hTERT-1007 and subcloned, in-frame, at the EcoRI site in the expression vector pVP22-1090 (Invitrogen). The resulting clone was named pVP22-hTERT-1091, as shown in FIG. 1. In FIG. 1, the black arrows within the circular map represent the VP22 and hTERT coding regions that will be expressed as a chimeric fusion protein. The backbone plasmid (pVP22 plasmid) was purchased from InVitrogen.

Generation of p1091/BHK Stable Cell Line. The pVP22-hTERT-1091 expression vector was stably transfected into BHK cells by using Lipofectamine Plus (Gibco Life-Technology). Briefly, the selection drug G418 was added to the transfected BHK cells 24 hours after transfection. Stably transfected p1091/BHK cells were grown in fibroblast growth media (DMEM plus 10% FBS) and 1 mg/ml of G418 for 2 weeks. One million of p1091/BHK cells were seeded in one T-75 flask and pulsed two times with 12 ml of DMEM plus 10% FBS for 24 hours. The collected, conditioned media were filter-sterilized through a Nunc 0.22 µm-filter and overlaid on to primary human fibroblasts, MDX1 (Modex thérapeutiques SA), at 50,000 cells per well in a 6-well plate. Final concentrations of fibroblast growth media were either 25%, 50%, 75%, or 100%. After the first 24 hours of exposure to the p1091/BHK conditioned media, the media were removed and replaced with the second batch of a 24-hour pulsed p1091/BHK conditioned media. After the second 24-hour exposure, MDX1 cells were harvested by trypsinization and pelleted.

Telomerase Assay. The Telomeric Repeat Amplification Protocol (TRAP) assay was performed according to the manufacturer's protocol (TRAPeze Telomerase Detection Kit, Oncor). Briefly, a pellet of 50,000 cells was resuspended in 50 µl of 1× CHAP lysis buffer containing RNaseOut at 200 U/ml (Gibco Life-Technology). The cell suspension was incubated on ice for 30 minutes and immediately centrifuged at 15,000 RPM at 4° C. for 15 minutes. T supernatant was immediately transferred to an RNase-Free Eppendorf tube. According to the manufacturer's protocol, the cell extract was diluted 1:10 so that a cell extract from 200 cells was used for the TRAP assay. Ten microliters of the reaction mix were resolved via 12.5% non-denaturing PAGE in 0.5× TBE buffer at 150 volts for 2 hours. The DNA ladders were visualized by staining in SYBR Green Stain (Molecular Probe).

Results. MDX1 primary human fibroblasts do not possess detectable telomerase enzyme activity as monitored by the TRAP assay. Thus, any detected telomerase enzyme activity from the MDX1 cells exposed to the conditioned media from pVP22-hTERT-1091/BHK can be attributed to the chimeric VP22-hTERT proteins that had been secreted by the stable pVP22-hTERT-1091/BHK cells and subsequently taken up by the primary human fibroblast MDX1 cells. PAGE results showed the telomerase activities from MDX1 cells that were exposed to the conditioned media from pVP22-hTERT-1091/BHK cells. The positive ladder formation in the 50% media mix indicated that the chimeric VP22-hTERT secreted from the pVP22-hTERT-1091/BHK cells was taken up by the primary human fibroblast MDX1.

EXAMPLE 2

Transient Immortalization Technology

The goal of this EXAMPLE is to validate the feasibility of chimeric protein translocation systems for the transient immortalization of primary human cells.

Construction of VP22-hTERT Fusion Cassettes and Expression Vectors: The basic VP22 expression vector was purchased from Invitrogen and renamed as pVP22-(cMyc-HIS-TAG)-1091. The cMyc and HIS denote the cMyc-tags and HIS-tags that are fused at the C-terminus of the VP22. The first gene to be fused to the VP22 was chosen to be the hTERT that was used successfully to enhance the proliferative potential of the primary human fibroblasts. Due to the concern that the C-terminal tags might interfere the hTERT catalytic activity, it was decided to make two VP22-hTERT fusion cassettes: (1) VP22-hTERT contains an in-frame fusion between VP22 and hTERT with no cMyc and HIS tags at the C-terminus of the fusion protein and (2) VP22-hTERT(cMyc-HIS-TAG) contains an in-frame fusion between VP22 and hTERT with cMyc and HIS tags at the C-terminus of the fusion protein. The cMyc and HIS tags were included at the N-terminus due to the need to identify the fusion protein inside mammalian cells and to be able to purify the fusion protein in large quantities.

The 3.4-kb EcoRI insert containing the hTERT was excised out of the p1007 and subcloned into the pVP22-cMyc-HIS-1090 at the EcoRI site resulting in an in-frame fusion between the N-terminal VP22 and the C-terminal hTERT. This new construct was named pVP22-hTERT-1091 (see, TABLE 1).

TABLE 1

A list of VP22-based fusion genes. (cMyc-HIS-TAG) denotes the cMyc-epitope and HIS-epitope tags fused in-frame at the C-terminus of the VP22, VP22-hTERT, and VP22-cMyc fusion genes.

| Plasmid | Expression Cassette Description | Sequence Verified | Western | ICC | TRAP |
|---|---|---|---|---|---|
| 1091 | VP22-hTERT | + | − | + | + |
| 1095 | VP22-hTERT-(cMyc-HIS-TAG) | + | + | + | + |
| 1101 | VP22-cMyc-(HIS-TAG) | + | + | + | − |

To generate the VP22-hTERT(cMyc-HIS-TAG) fusion protein, we removed the termination codon TGA at the end of the hTERT coding sequence. Briefly, the 3' 900-bp MluI/NotI fragment in hTERT was regenerated by PCR using oligonucleotides in order to generate a 3' 900-bp MluI/NotI fragment containing no TGA termination codon. This 3' 900-bp MluI/NotI hTERT PCR produced with no TGA termination codon was cloned directly into pCR2.1-TOPO cloning vector and the resulting plasmid was named as pCR2.1-TOPO-hTERT(−)TGA-1093. The nucleotide validity of the PCR insert in p1093 was confirmed to be 100% accurate by nucleotide sequencing reactions. The 3' 900-bp MluI/NotI fragment in pVp22-hTERT-1091 was substituted with the one from p1093 resulting in an in-frame fusion of VP22, hTERT, cMyc epitope tag, and HIS epitope tag. The resulting expression vector was named as pVP22-hTERT-(cMyc-HIS-Tag)-1095.

Construction of VP22-cMyc Fusion Cassettes and Expression Vectors: The VP22-cMyc fusion cassette contains only HIS-tag at the C-terminus of the fusion protein. In order to easily fuse in-frame the VP22 and cMyc coding sequences, the entire cMyc coding sequence was regenerated in a 5' 790-bp and 3' 549-bp fragments by resulting in pCR2.1-cMyc-PCR1-1097 and -1099, respectively. The nucleotide validity of the PCR inserts in p1097 and p1099 was confirmed to be 100% accurate by nucleotide sequencing reactions. The 5' 790-bp and 3' 549-bp cMyc fragments were combined by subcloning the 3' 549-bp ClaI/BamHI from p1099 into the ClaI/BamHI site in the p1097 generating a full-length cMyc without a TGA termination codon. This plasmid was named as pCR2.1-TOPO-cMyc-(−)TGA-1100. Subsequently, the full-length cMyc without the TGA termination codon was subcloned out of p 1100 by EcoRI and NotI restriction digestion and into p1090 generating pVP22-cMyc-HIS-1101.

Figure 2:
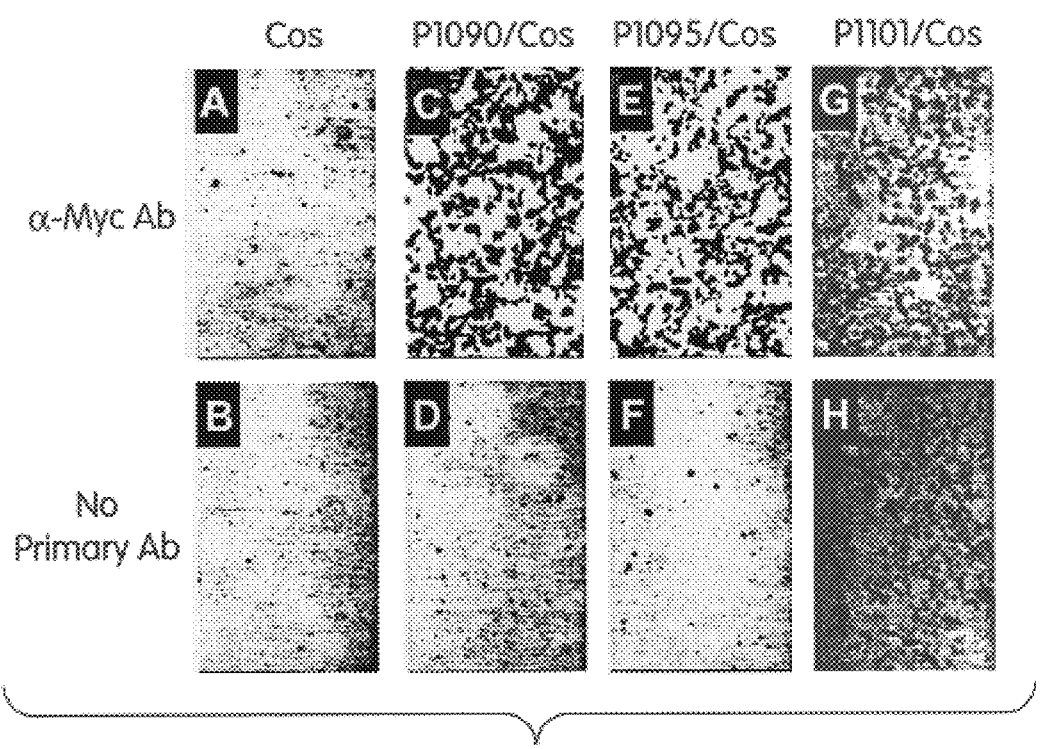
FIG. 2 is a depiction of a set of illustrations showing the detection of VP22-hTERT and VP22-cMyc chimera proteins by immunocytochemistry (ICC).

Detection of VP22-hTERT and VP22-cMyc Fusion Proteins by ICC Analysis: To demonstrate that the VP22-hTERT and Vp22-cMyc fusion genes were properly constructed, immunocytochemistry (ICC) analysis was performed on COS cells that were transiently transfected with either p1095 or p1101. The control with no DNA plasmid (see, FIG. 2, Panels A and B) and the control VP22 vector pVP22-(cMyc-HIS-TAG)-1090 was included (see, FIG. 2, Panels C and D). Since VP22, hTERT and cMyc are nuclear proteins, clear nuclear staining of p1090, p1095- and p1101- transiently transfected was clearly demonstrated by ICC using anti-cMyc antibodies. This data also showed that the fusion VP22-hTERT (see, FIG. 2, Panels E and F) and VP22-cMyc (see, FIG. 2, Panels G and H) fusion genes were correctly constructed and the respective fusion proteins were properly synthesized and transported to the nucleus as expected of nuclear proteins. Results in FIG. 2 were obtained by transiently transfecting Cos cells with no plasmid DNA (Panels A and B), pVP22-(cMyc-HIS-TAG)-1090 control vector (Panels C and D), pVP22-hTERT-(cMyc-HIS-TAG)-1095 vector (Panels E and F), and pVP22-cMyc-(HIS-TAG)-1101 vector (Panels G and H). Primary anti-cMyc antibody (c-Myc Ab) was added in Panels A, C, E, and G whereas no primary anti-cMyc antibody was added in Panels B, D, F, and H.

Figure 3:
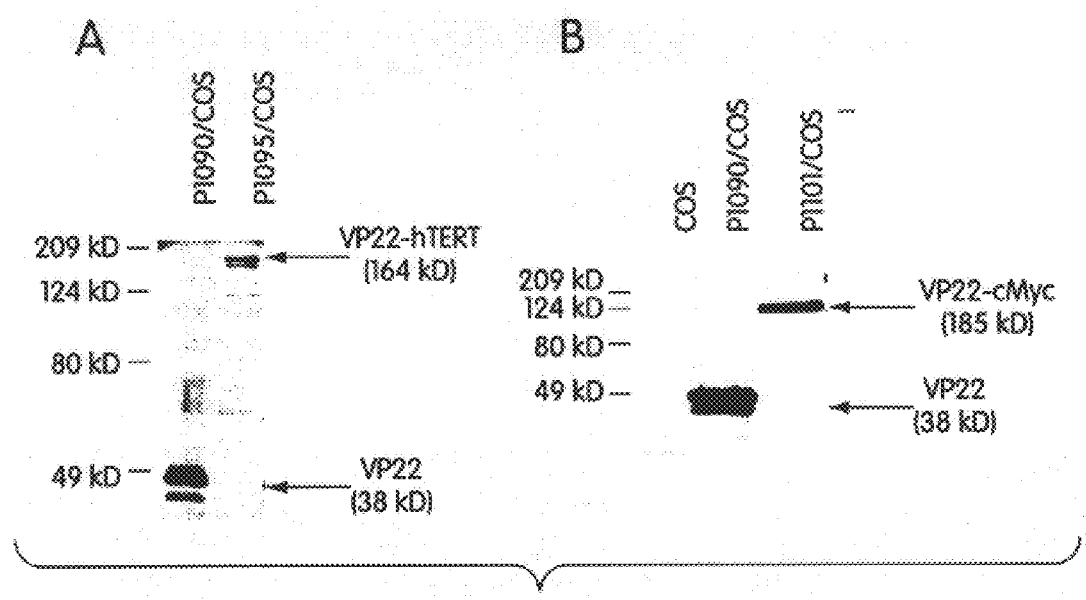
FIG. 3 is a Western blot analysis of VP22-based chimera proteins expressed in COS, wherein Panel A depicts the VP22-hTERT-(cMyc-HIS-TAG) fusion protein and Panel B depicts the VP22-cMyc-(HIS-TAG) fusion protein.

Detection of VP22-hTERT and VP22-cMyc Fusion Proteins by Western Blot Analysis: To demonstrate that the VP22-hTERT and Vp22-cMyc fusion proteins were of the correct molecular weight sizes, we performed Western blot analysis on total cell lysates from COS cells that were transiently transfected with either p1095 or p1101. The fusion proteins with the expected molecular weights were clearly detected by anti-cMyc antibodies, thus, further validating that the fusion VP22-hTERT (see, FIG. 3, Panel A) and VP22-cMyc (see, FIG. 3, Panel B) fusion genes were constructed correctly. In FIG. 3 Panel A, the VP22-hTERT-(cMyc-HIS-TAG) fusion protein and the control VP22-(cMyc-HIS-TAG) protein in expression vectors p1095 and p1090, respectively, were expressed in transiently transfected COS cells. The primary antibody used was the anti-cMyc antibody from Invitrogen. In FIG. 3 Panel B, the VP22-cMyc-(HIS-TAG) fusion protein and the control VP22-(cMyc-HIS-TAG) protein in expression vectors p1101 and p1090, respectively, were expressed in transiently transfected COS cells. The primary antibody used was the anti-cMyc antibody from Invitrogen. The arrows molecular weights of VP22-hTERT-(cMyc-HIS-TAG), VP22-cMyc-(HIS-TAG), and TAG).

Figure 4A:
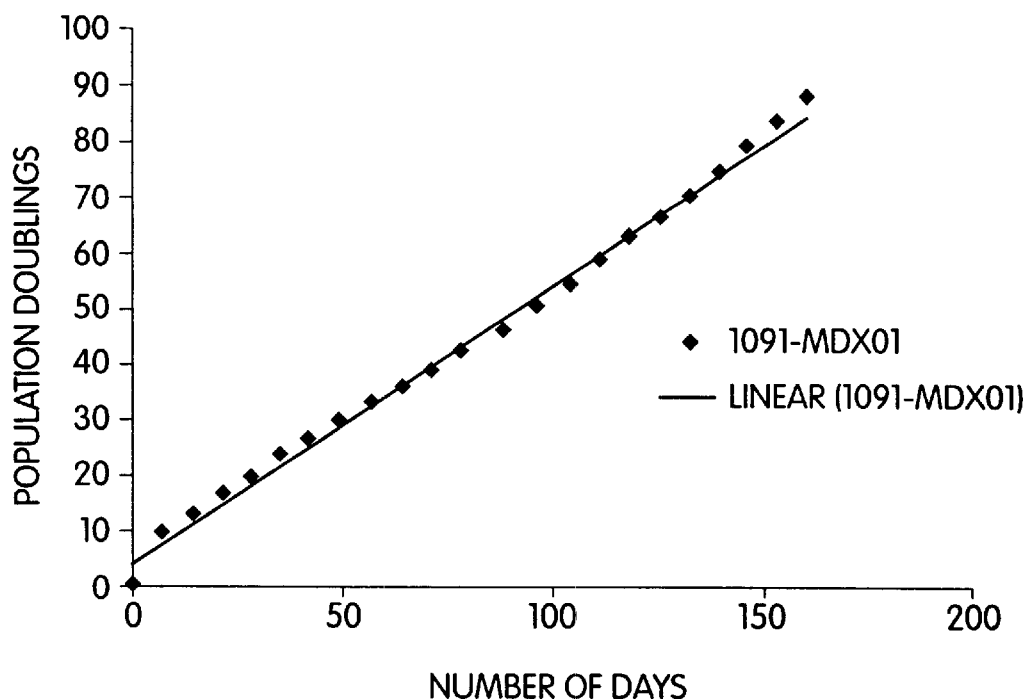
FIG. 4A is a graphic depiction of the population doubling curve for 1091-MDX01 cell lines.
Figure 4B:
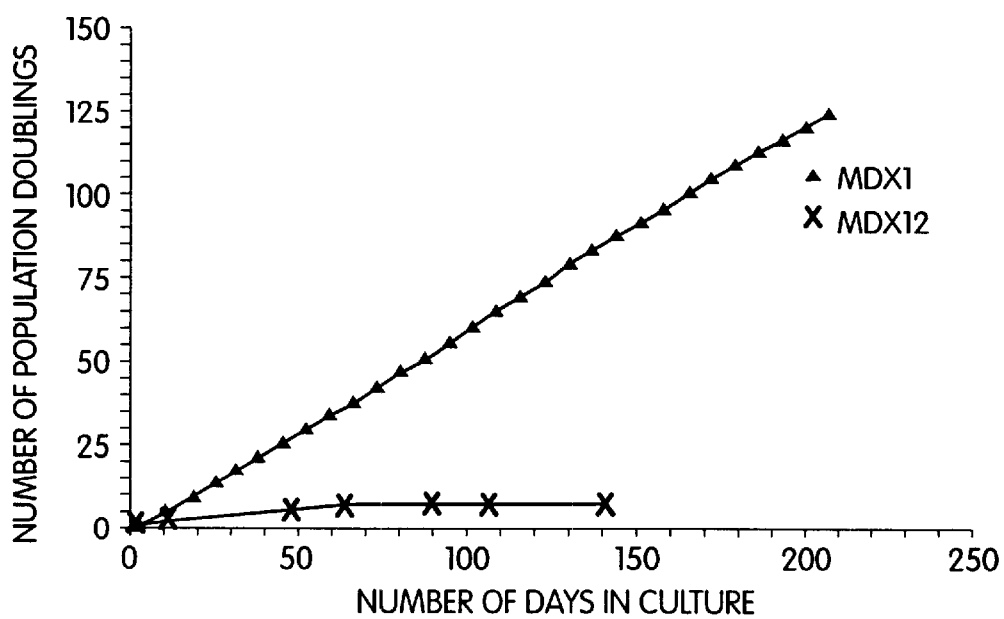
FIG. 4B is a graphic depiction of. the population doubling curve for mMLV-hTERT immortalized MDX12 ("x" curve) cells compared to the parent primary MDX1 cells (diamond curve) as determined by repetitive serial passaging of the VP22-hTERT cell line.

Demonstration of enhanced proliferation capacity: The VP22-hTERT stably transfected cell line demonstrates a fully immortalized phenotype as evidenced by the enhanced population doubling curve depicted in FIG. 4. FIG. 4A shows the population doubling curve for 1091-MDX01 as determined by repetitive serial passaging of the VP22-hTERT cell line. FIG. 4B shows the population doubling curve for mMLV-hTERT immortalized MDX12 ("x" curve) compared to the parent primary MDX1 cell (diamond curve) as determined by repetitive serial passaging of the VP22-hTERT cell line. Normal non-immortalized primary MDX01 cells demonstrate 13–20 PD's under the same culture conditions.

Demonstration of the Catalytic Enzyme Activity by VP22-hTERT Fusion Proteins: To demonstrate that the N-terminal VP22 fusion protein did not affect the catalytic activity of the C-terminal fused hTERT enzyme, TRAP enzyme assays were performed on total cell extracts from telomerase negative MDX1 cells that were transiently transfected with either p1091 or p1095. Both p1091 and p1095 exhibited clear ladder formation clearly indicating the preservation of the telomerase catalytic activity in the VP22-hTERT fusion proteins (see, FIG. 4A).

Figure 5A:
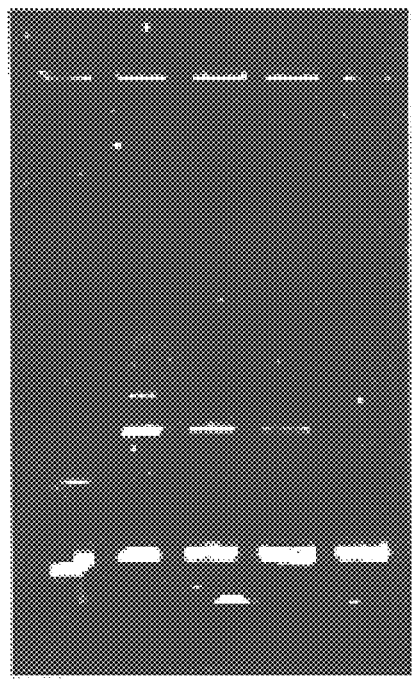
FIGS. 5A and 5B are a set of illustrations of a set of gels showing the telomerase catalytic activities of VP22-hTERT chimera proteins as demonstrated by TRAP, in COS cells transiently transfected with VP22, VP22-hTERT, and VP22-hTERT-(cMyc-HIS-TAG) fusion constructs (FIG. 5A) or in stable polyclonal p1091/MDX1 cells, with MDX1 as a negative control, and MDX12 as a positive control (FIG. 5B).
Figure 5B:
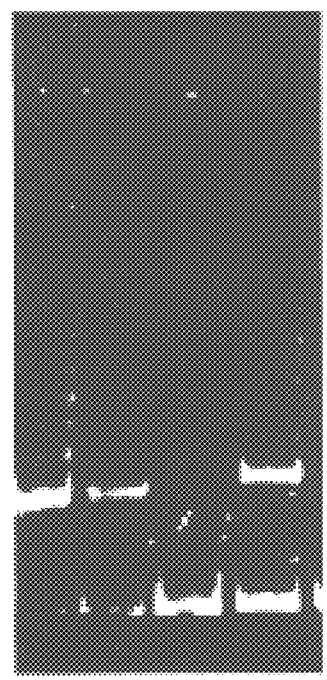
Figure 6A:
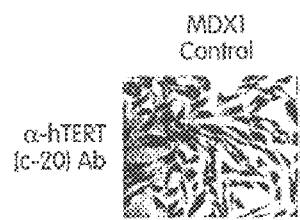
FIGS. 6A–6F are a set of illustrations showing the detection of the presence of telomerase in p1091/MDX1 by immunocytochemistry ("ICC").
Figure 6C:
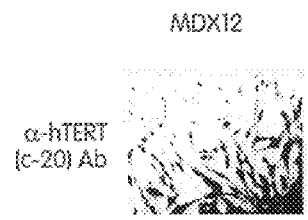
Figure 6E:
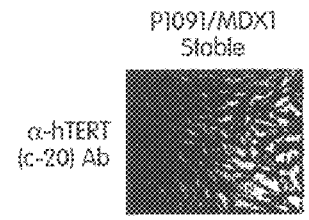
Figure 6B:
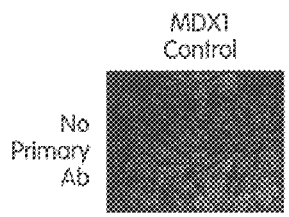
Figure 6D:
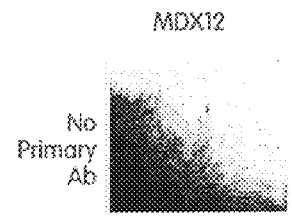
Figure 6F:
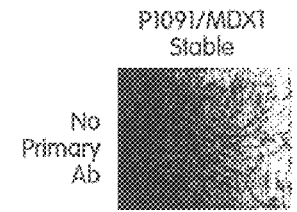

To determine if VP22-hTERT fusion protein encoded by expression plasmid p1091 was capable of immortalizing telomerase negative primary human fibroblast cell lines these constructs were stably transfected into hTERT-negative MDX1 cells. After 5 weeks of G418 selection at 50 ng/ml, a small colony of G418-resistant p1091/MDX1 was selected and expanded for further population doubling studies. TRAP assay on p1091/MDX1 clearly showed the hTERT enzyme activity (see, FIG. 5B). In FIG. 5A, TRAP assay was performed on cell lysates from COS cells transiently transfected with VP22, VP22-hTERT, and VP22-hTERT-(cMyc-HIS-TAG) fusion constructs in expression vectors p1090, p1091, and p1095, respectively. 293T was included as positive control for hTERT catalytic activities in TRAP. In FIG. 5B, TRAP assay was performed on stable polyclonal p1091/MDX1 cells, MDX1 as negative control, and MDX12 as positive control.

Furthermore, ICC using anti-hTERT antibodies clearly demonstrated positive nuclear staining in p1091/MDX1 cells (see, FIG. 6A through FIG. 6F). ICC was performed on p1091/MDX1 stable cells with anti-hTERT antibody, -hTERT(C-20) Ab, while MDX1 (FIG. 6A and 6B) and MDX12 (FIG. 6C and FIG. 6D) cells were used as hTERT-negative and hTERT-positive controls, respectively. Primary anti-hTERT antibody was added in 6A, 6C, and 6E whereas no primary anti-hTERT antibody was added in 6B, 6D, and 6F. These results confirm the presence of "telomerase" proteins in p1091/MDX1 and are consistent with the detection of telomerase activities in p 1091/MDX1 by TRAP assays. P1091/MDX1 stable cells were shown to be G418-resistant but Hygromycin-sensitive demonstrating that they are not "contaminant" cells derived from MDX12 line which is a Hygromycin-resistant mMMLV hTERT immortalized fibroblast positive control cell line.

Figure 7:
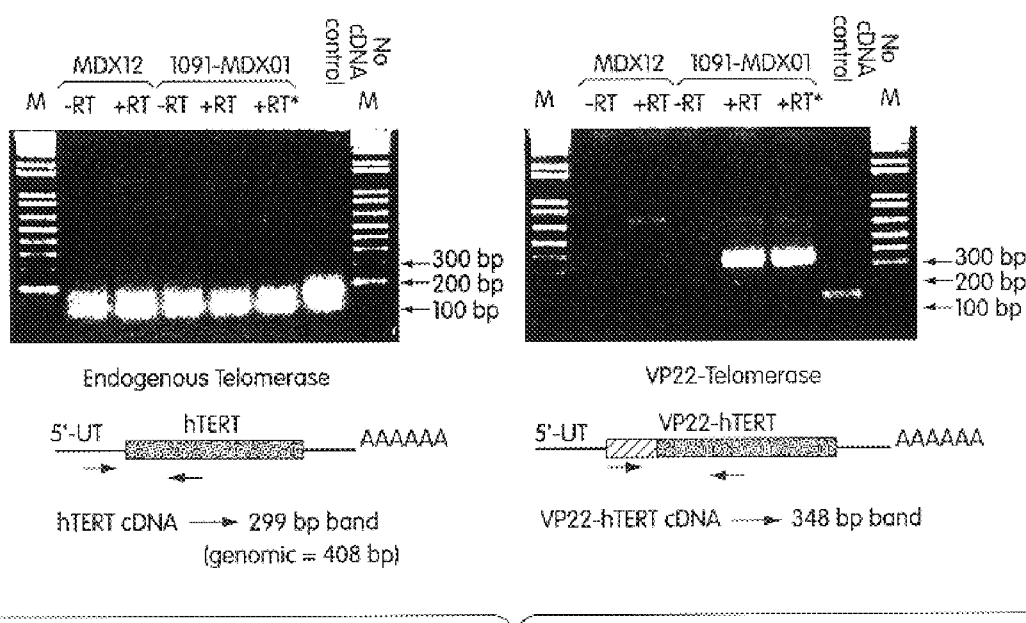
FIG. 7 is a set of illustrations showing endogenous hTERT and VP22-hTERT mRNA expression as measured by RT-PCR in MDX12 and 1091-MDX01 immortalized cell lines.

However, there is still a possibility that the p1091/MDX1 cells are derived from spontaneously transformed MDX 1 cells instead of being truly immortalized due to the forced expression of VP22-hTERT fusion proteins. To resolve this issue, RT-PCR analysis was performed on total mRNA isolated from MDX01, p1091-MDX01 (VP22-hTERT immortalized), and MDX12 (mMLV-hTERT immortalized) cell lines. As shown in the left hand side of FIG. 7, RT-PCR was performed on mRNA isolated from MDX12 (hTERT immortalized) and 1091-MDX01 (VP22-hTERT immortalized)cell lines using oligonucleotides specific for endogenous hTERT mRNA expression. As shown in the right hand side of FIG. 7, RT-PCR was performed on mRNA isolated from MDX12 (hTERT immortalized) and 1091-MDX01 (VP22-hTERT immortalized) cell lines using oligonucleotides specific for VP22-hTERT mRNA expression (FIG. 7B). +RT signifies addition of reverse transcriptase and –RT signifies PCR without reverse transcriptase addition; +RT* indicates use of a different brand of reverse transcriptase. As shown in FIG. 7, when RT-PCR is performed using an oligonucleotide pair specific for the 5' untranslated portion and the coding regions of the endogenous hTERT gene, no PCR signal is obtained from the mMLV-hTERT or VP22-hTERT immortalized cell lines. When RT-PCR is performed with a pair of oligonucleotides specific for the VP22 and hTERT coding regions only the VP22-hTERT immortalized 1091-MDX01 cell line is positive.

Figure 8:
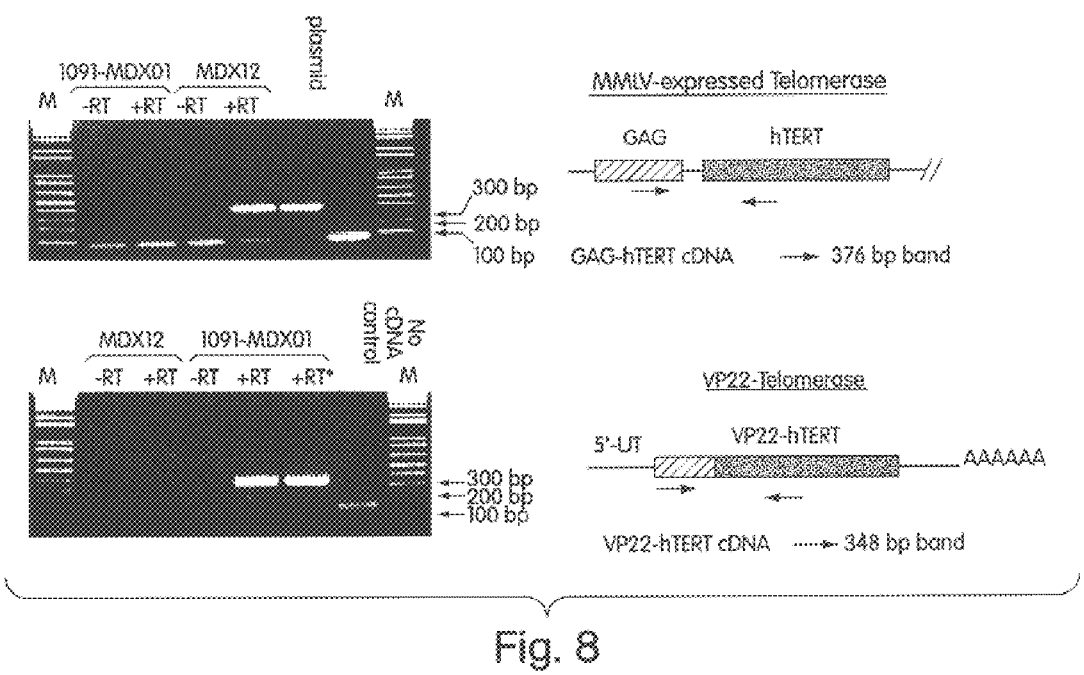
FIG. 8 is a set of illustrations showing endogenous hTERT and VP22-hTERT mRNA expression as measured by RT-PCR in MDX12 and 1091-MDX01 immortalized cell lines.

Furthermore, in FIG. 8A, further confirms that when RT-PCR is performed using oligonucleotide pairs specific to the mMLV and hTERT coding regions only the mMLV-hTERT immortalized MDX12 cell line demonstrates a positive signal. In FIG. 8, RT-PCR was performed on mRNA isolated from MDX12 (hTERT immortalized) and 1091-MDX01 (VP22-hTERT immortalized) cell lines using oligonucleotides specific for mMLV-hTERT mRNA expression (FIG. 8, top). RT-PCR was performed on mRNA isolated from MDX12 (hTERT immortalized) and 1091-MDX01 (VP22-hTERT immortalized)cell lines using oligonucleotides specific for VP22-hTERT mRNA expression (FIG. 8, bottom). +RT signifies addition of reverse transcriptase and -RT signifies PCR without reverse transcriptase addition; +RT* indicates use of a different brand of reverse transcriptase.

Thus, the identity of the telomerase enzyme activity as detected by TRAP on p1091/MDX01 cell extracts can be attributed to the VP22-hTERT fusion mRNA and not to endogenously activated hTERT proteins. This demonstrates that similar to MDX01 cells immortalized with constitutively expressed mMLV-hTERT the VP22-hTERT immortalized 1091-MDX01 is also fully immortalized by the expression of the VP22-hTERT fusion mRNA and hence protein.

In summary:

1. The VP22-hTERT, VP22-hTERT-(cMyc-HIS-TAG), and VP22-cMyc-(HIS-TAG) fusion genes were verified by sequencing reactions to be free of sequence mistakes and to be correctly in-frame fused between the VP22 and hTERT coding domains, or VP22, hTERT, cMyc-TAG, and HIS-TAG coding domains, or VP22, cMyc, and HIS-TAG coding domains, respectively.

2. The VP22-hTERT, VP22-hTERT-(cMyc-HIS-TAG), and VP22-cMyc-(HIS-TAG) fusion genes are all capable of expressing intact fusion proteins as demonstrated by ICC and Western blot analysis from transiently transfected COS cells.

3. The telomerase catalytic activities of VP22-hTERT and VP22-hTERT-(cMyc-HIS-TAG) fusion proteins were conclusively demonstrated in vitro by TRAP assays.

4. The expression of VP22-hTERT mRNA by RT-PCR and the immortalized phenotype by population study analysis, successfully demonstrates that the VP22-hTERT fusion protein is functional with respect to primary fibroblast cell immortalization.

EQUIVALENTS

Although particular embodiments have been disclosed herein in detail, this has been done by way of example for purposes of illustration only, and is not intended to be limiting as to the precise form of the disclosed invention or to the scope of the appended claims which follow. In particular, various substitutions, alterations, and modifications known to persons skilled in the art may be made to the invention without departing from the spirit and scope of the invention as defined by the claims.

We claim:

1. A fusion polypeptide, comprising:
   (i) a first part comprising a translocation moiety, said translocation moiety comprising a transport function, said translocation moiety selected from the group consisting of:
      (a) a polypeptide comprising a herpesviral VP22 protein;
      (b) a polypeptide comprising a human immunodeficiency virus (HIV) TAT protein;
      (c) a polypeptide comprising a homeodomain of an Antennapedia protein (Antp HD);
      (d) a polypeptide comprising an Arginine repeat (Arg repeat); and
      (e) a cationic polymer; and
   (ii) a second part comprising a polypeptide selected from the group consisting of:
      (a) a polypeptide having cell immortalization activity,
      (b) a polypeptide that synthesizes telomeric DNA at chromosomal ends, and
      (c) a polypeptide which is a transcriptional activator of telomerase activity resulting in synthesis of telomeric DNA at chromosomal ends.

2. The fusion polypeptide of claim 1, wherein the polypeptide having cell immortalization activity is selected from the group consisting of: SV40 small T antigen, SV40 large T antigen, adenovirus E1A, papilloma virus E6, papilloma virus E7, Epstein-Barr virus, Epstein-Barr nuclear antigen-2, human T-cell leukemia virus-1 (HTLV-1), HTLV-1 tax, herpesvirus saimiri, mutant p53, myc, c-jun, c-ras, c-Ha-ras, h-ras, v-src, c-fgr, myb, c-myc, n-myc, v-myc, and Mdm2.

3. The fusion polypeptide of claim 1, wherein the polypeptide that synthesizes telomeric DNA at chromosomal ends is selected from the group consisting of telomerase, telomerase reverse transcriptase (TERT), p140, p105, p48, and p43.

4. A method of transiently immortalizing a cell comprising the step of:
   (a) expanding the cell in growth medium containing:
      (i) a first part comprising a translocation moiety, said translocation moiety comprising a transport function, said translocation moiety selected from the group consisting of:

(a) a polypeptide comprising a herpesviral VP22 protein;
(b) a polypeptide comprising a human immunodeficiency virus (HIV) TAT protein;
(c) a polypeptide comprising a homeodomain of an Antennapedia protein (Antp HD);
(d) a polypeptide comprising an Arginine repeat (Arg repeat); and
(e) a cationic polymer; and
(ii) a second part comprising a polypeptide having cell immortalization activity; wherein
(b) the fusion protein is taken up by the cell to result in proliferation of the cell; and
(c) wherein growing the immortalized cell in growth medium that does not contain the fusion protein terminates the proliferative effects of the fusion protein.

5. The method of claim 4, wherein the second polypeptide having cell immortalization activity is selected from the group consisting of: SV40 small T antigen, SV40 large T antigen, adenovirus E1A, papilloma virus E6, papilloma virus E7, Epstein-Barr virus, Epstein-Barr nuclear antigen-2, human T-cell leukemia virus-1 (HTLV-1), HTLV-1 tax, herpesvirus saimiri, mutant p53, myc, c-jun, c-ras, c-Ha-ras, h-ras, v-src, c-fgr, myb, c-myc, n-myc, v-myc, and Mdm2.

6. A method of transiently increasing the replicative capacity of a cell comprising of the steps of:
(a) exposing the cell to growth medium containing a fusion protein comprising:
(i) a first part comprising a translocation moiety, said translocation moiety comprising a transport function, said translocation moiety selected from the group consisting of:
(a) a polypeptide comprising a herpesviral VP22 protein;
(b) a polypeptide comprising a human immunodeficiency virus (HIV) TAT protein;
(c) a polypeptide comprising a homeodomain of an Antennapedia protein (Antp HD);
(d) a polypeptide comprising an Arginine repeat (Arg repeat); and
(e) a cationic polymer; and
(ii) a second part comprising a polypeptide that synthesizes telomeric DNA at chromosomal ends; then
(b) exposing the cell to growth medium that does not contain the fusion protein of step (a);
(c) wherein growing the cell in growth medium that does not contain the fusion protein terminates the replicative capacity-increasing effects of the fusion protein.

7. The method of claim 6, wherein the second polypeptide is selected from the group consisting of: telomerase, telomerase reverse transcriptase (TERT), p140, p105, p48, and p43.

8. A method of transiently proliferating a cell and increasing the replicative capacity of such cell comprising of the steps of:
(I) expanding the cell in growth medium containing:
(A) a first fusion protein comprising:
(i) a first part comprising a translocation moiety, said translocation moiety comprising a transport function, said translocation moiety selected from the group consisting of:
(a) a polypeptide comprising a herpesviral VP22 protein;
(b) a polypeptide comprising a human immunodeficiency virus (HIV) TAT protein;
(c) a polypeptide comprising a homeodomain of an Antennapedia protein (Antp HD);
(d) a polypeptide comprising an Arginine repeat (Arg repeat); and
(e) a cationic polymer; and
(ii) a second part comprising a polypeptide having cell immortalization activity; and
(B) a second fusion protein comprising:
(i) a first part comprising a translocation moiety, said translocation moiety comprising a transport function, said translocation moiety selected from the group consisting of:
(a) a polypeptide comprising a herpesviral VP22 protein;
(b) a polypeptide comprising a human immunodeficiency virus (HIV) TAT protein;
(c) a polypeptide comprising a homeodomain of an Antennapedia protein (Antp HD);
(d) a polypeptide comprising an Arginine repeat (Arg repeat); and
(e) a cationic polymer; and
(ii) a second part comprising a polypeptide that synthesizes telomeric DNA at chromosomal ends; then
(II) exposing the cell to growth medium that does not contain the fusion proteins of step (I); wherein
(III) growing the cell in growth medium of step (II) terminates the replicative capacity-increasing effects of the fusion proteins.

9. The method of claim 8, wherein the polypeptide having cell immortalization activity is selected from the group consisting of: SV40 small T antigen, SV40 large T antigen, adenovirus E1A, papilloma virus E6, papilloma virus E7, Epstein-Barr virus, Epstein-Barr nuclear antigen-2, human T-cell leukemia virus-1 (HTLV-1), HTLV-1 tax, herpesvirus saimiri, mutant p53, myc, c-jun, c-ras, c-Ha-ras, h-ras, v-src, c-fgr, myb, c-myc, n-myc, v-myc, and Mdm2.

10. The method of claim 8, wherein the second polypeptide is selected from the group consisting of: telomerase, telomerase reverse transcriptase (TERT), p140, p105, p48, and p43.

11. A cell culture medium containing at least one fusion protein of claim 1.

12. A production cell that expresses at least one fusion protein of claim 1.

* * * * *

SEQUENCE LISTING

```
<160> NUMBER OF SEQ ID NOS: 8

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: PCR PRIMER

<400> SEQUENCE: 1
atatatgcta gcgccaccat gccgcgcgct ccccgctgcc                           40

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: PCR PRIMER

<400> SEQUENCE: 2
atatatgaat tcagtccagg atggtcttga agtctgaggg c                         41

<210> SEQ ID NO 3
<211> LENGTH: 5
<212> TYPE: PRT
<213> ORGANISM: Herpes simplex type 1 virus

<400> SEQUENCE: 3

Arg Ser Ala Ser Arg
  1               5

<210> SEQ ID NO 4
<211> LENGTH: 5
```

-continued

```
<212> TYPE: PRT
<213> ORGANISM: Herpes simplex type 1 virus

<400> SEQUENCE: 4

Arg Thr Ala Ser Arg
  1               5

<210> SEQ ID NO 5
<211> LENGTH: 5
<212> TYPE: PRT
<213> ORGANISM: Herpes simplex type 1 virus

<400> SEQUENCE: 5

Arg Ser Arg Ala Arg
  1               5

<210> SEQ ID NO 6
<211> LENGTH: 5
<212> TYPE: PRT
<213> ORGANISM: Herpes simplex type 1 virus

<400> SEQUENCE: 6

Arg Thr Arg Ala Arg
  1               5

<210> SEQ ID NO 7
<211> LENGTH: 5
<212> TYPE: PRT
<213> ORGANISM: Herpes simplex type 1 virus

<400> SEQUENCE: 7

Ala Thr Ala Thr Arg
  1               5

<210> SEQ ID NO 8
<211> LENGTH: 6
<212> TYPE: PRT
<213> ORGANISM: Herpes simplex type 1 virus

<400> SEQUENCE: 8

Arg Ser Ala Ala Ser Arg
  1                   5
```